(12) United States Patent
Drent et al.

(10) Patent No.: US 6,984,755 B2
(45) Date of Patent: Jan. 10, 2006

(54) PROCESSES FOR THE PREPARATION OF A CARBOXYLIC ANHYDRIDE AND USE OF THE CARBOXYLIC ANHYDRIDE AS AN ACYLATION AGENT

(75) Inventors: Eit Drent, Amsterdam (NL); Renata Helena Van Der Made, Amsterdam (NL); Robert Ian Pugh, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/504,913

(22) PCT Filed: Feb. 18, 2003

(86) PCT No.: PCT/EP03/01689

§ 371 (c)(1),
(2), (4) Date: Nov. 8, 2004

(87) PCT Pub. No.: WO03/070679

PCT Pub. Date: Aug. 28, 2003

(65) Prior Publication Data

US 2005/0059841 A1   Mar. 17, 2005

(30) Foreign Application Priority Data

Feb. 19, 2002   (EP) ............................................ 02251114

(51) Int. Cl.
*C07C 51/56*   (2006.01)

(52) U.S. Cl. ...................................... 562/891; 562/890
(58) Field of Classification Search ................. 562/891, 562/890

See application file for complete search history.

(56) References Cited

U.S. PATENT DOCUMENTS

| | | | |
|---|---|---|---|
| 4,786,443 A | * | 11/1988 | Drent et al. ................. 562/890 |
| 6,156,934 A | | 12/2000 | Suykerbuyk et al. .......... 568/12 |
| 2001/0051745 A1 | | 12/2001 | Pearson et al. ............. 560/207 |

FOREIGN PATENT DOCUMENTS

| | | |
|---|---|---|
| DE | 32511 | 10/1964 |
| DE | 1966944 | 6/1975 |
| DE | 10023470 | 11/2001 |
| DE | 10037961 | 2/2002 |
| WO | 98/42717 | 10/1998 |
| WO | 01/28972 | 4/2001 |
| WO | 01/72697 | 10/2001 |
| WO | 01/85662 | 11/2001 |

OTHER PUBLICATIONS

International Search Report dated Jun. 24, 2003.
Robert I. Pugh, et al, "Tandem isomerisation–carbonylation catalysis: highly active palladium (ii) catalysts for the selective methoxycarbonylation of internal alkenes to linear esters", Chemcomm Commun. 2001, pp. 1476–1477.
Ullman's Encyclopedia of Ind. Chem, 5$^{th}$ edition, 1986, vol. A5: "Cancer chemotherapy to ceramic colarants", pp. 222–223.
Robert Pugh, "Phospha–adamantanes a new class of bulky alkyl phosphine ligands", (thesis submitted to the University of Bristol, Apr. 2000) pp. 50–76.
Robert Pugh, et al., "Bis (phospha–adamantyl) alkanes:a new class of very bulky diphosphines", ChemComm, pp. 901–90226 Mar. 1996.
British Thesis by Joanne H. Downing, "Precious Metal Complexes of some novel functionalized secondary and tertiary phosphines", University of Bristol, Nov. 1992.
U.S. Appl. No. 10/505,019, filed Aug. 18, 2004, Drent et al.

\* cited by examiner

*Primary Examiner*—Paul A. Zucker

(57) ABSTRACT

A process for the preparation of an carboxylic anhydride by reaction of an ethylenically unsaturated compound with carbon monoxide and an carboxylic acid in the presence of a catalyst involving:
a) a source of a group VIII metal;
b) a bidentate diphosphine of formula I,

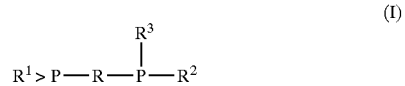

(I)

wherein $R^1$ represents a bivalent radical that together with the phosphorus atom to which it is attached is an optionally substituted 2-phospha-tricyclo[3.3.1.1 {3,7}]-decyl group or a derivative thereof in which one or more of the carbon atoms are replaced by heteroatoms ("2-PA" group); wherein $R^2$ and $R^3$ independently represent univalent radicals of up to 20 atoms or jointly form a bivalent radical of up to 20 atoms; and
wherein R represents a bivalent organic bridging group; and,
c) a complexing anion; wherein the complexing anion is the anion of the carboxylic acid. A process wherein the carboxylic acid is prepared in-situ and use of the carboxylic anhydride as an acylation agent.

9 Claims, No Drawings

PROCESSES FOR THE PREPARATION OF A CARBOXYLIC ANHYDRIDE AND USE OF THE CARBOXYLIC ANHYDRIDE AS AN ACYLATION AGENT

FIELD OF THE INVENTION

The present invention relates to a process for the preparation of a carboxylic anhydride by reaction of an ethylenically unsaturated compound with carbon monoxide and a carboxylic acid. In specific the present invention relates to a process for the preparation of propanoic anhydride.

BACKGROUND OF THE INVENTION

WO-A-9842717 describes in its examples the carbonylation of ethylenically unsaturated compounds, viz. ethene, propene, $C_{14}$-olefin, methyl pentenoate and vinyl acetate, by reaction thereof with carbon monoxide and the hydroxyl-group containing compounds methanol and water. The reactions are carried out in the presence of a catalyst comprising palladium (II) acetate or platinum (II) acetylacetonenate; and 1,3-PP'-di(2-phospha-1,3,5,7-tetramethyl-6,9,10-trioxatri-cyclo[3.3.1.1{3.7}]decyl)propane (DPA3).

The catalyst used for reactions with methanol and water further comprises methyl sulphonic acid, a strong acid with a pKa<-1 when measured in water at a temperature of 18° C., as a source of anions. The methyl sulphonic acid is present in molar excess to the palladium or platinum cations.

Although, in passing, WO-A-9842717 mentions a variety of possible co-reactants, including also carboxylic acids, in the examples water and methanol are the only hydroxyl-group containing compounds used as a co-reactant.

It has been found that the use of a catalyst as exemplified in WO-A-9842717, containing methyl sulphonic acid, in such a process for the preparation of a carboxylic anhydride results in satisfactory reaction rates (see comparative example A). An improvement towards a higher reaction rate, however, would be very desirable.

SUMMARY OF THE INVENTION

Accordingly the present invention provides a process for the preparation of a carboxylic anhydride by reaction of an ethylenically unsaturated compound with carbon monoxide and a carboxylic acid in the presence of a catalyst comprising:
a) a source of a group VIII metal;
b) a bidentate diphosphine of formula I,

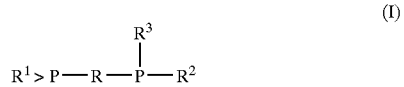

(I)

wherein $R^1$ represents a bivalent radical that together with the phosphorus atom to which it is attached is an optionally substituted 2-phospha-tricyclo[3.3.1.1{3,7})]-decyl group or a derivative thereof in which one or more of the carbon atoms are replaced by heteroatoms ("2-PA" group); wherein $R^2$ and $R^3$ independently represent univalent radicals of up to 20 atoms or jointly form a bivalent radical of up to 20 atoms; and wherein R represents a bivalent organic bridging group; and
c) a complexing anion;
wherein the complexing anion is the anion of the carboxylic acid.

DETAILED DESCRIPTION OF THE INVENTION

Without wishing to be bound to any theory, it is believed that in the examples of WO-A-9842717 and in comparative example A methyl sulphonic acid, being the strongest acid, protonates any anions of formed carboxylic acid. In the examples of WO-A-9842717 and in comparative example A the methyl sulphonic acid, and not any carboxylic acid formed, provides the complexing anion.

The process of the present invention results in high reaction rates. Moreover, the use of the anion of the carboxylic acid co-reactant as a complexing anion simplifies the preparation process.

WO-A-9842717 gives no indication that the carboxylic acid co-reactant could be used successfully as a simultaneous provider of the complexing anions in the catalyst. Moreover, WO-A-9842717 gives no indication that the use of the anions of the carboxylic acid as complexing anions would result in higher reaction rates.

On the contrary, WO-A-9842717 teaches the preferred use of a separate source of anions, preferably a strong acid such as methyl sulfonic acid, as a provider of the complexing anion.

Preferably the anions of the carboxylic acid and optionally any counter-anions in the source of group VIII metal are the main anions present. Anions of any additional acids "stronger" than the carboxylic acid co-reactant, i.e. acids having a pKa lower than that of the carboxylic acid in the used solvent, can be present, but only in small amounts. By small amounts is understood such amounts that the carboxylic acid co-reactant still acts as the main provider of the complexing anions. For practical reasons any additional "stronger" acid is therefore present in a molar ratio to the group VIII metal of less than 0.5:1, preferably less than 0.2:1, more preferably less than 0.1:1 and most preferably less than 0.01:1. Most preferably essentially no anions of such an additional "stronger" acid are present and most preferably the anions of the carboxylic acid and optionally any counter-anions in the source of group VIII metal are essentially the only anions present.

In the process according to the invention the ethylenically unsaturated compound is preferably an alkene having from 2 to 20, more preferably from 2 to 10, and most preferably from 2 to 4 carbon atoms. The alkene can be normal, branched or can comprise a cyclic structure. The alkene can comprise one or more double bonds per molecule and those double bonds can be internal or terminal. In the alkene one or more hydrogen atoms may have been replaced by other atoms, such as halogen atoms, sulphur atoms, oxygen atoms or nitrogen atoms, or by groups of atoms, such as hydroxyl groups; cyano groups; alkoxy groups, such as methoxy or ethoxy groups; thioxy groups; amino groups such as dimethyl- and diethyl-amino groups; or aromatic groups, such as phenyl, tolyl or naphthyl groups. Preferably the alkene contains no heteroatoms.

Examples of alkenes include ethene, propene, 1- or 2-butene, 1- or internal pentene, 1- or internal hexene, 1- or internal heptene, 1- or internal octene, 1- or internal decene, internal or terminal $C_{14}$–$C_{18}$ olefins, pentenenitrils, cyclohexene and styrene. Preferred alkenes include ethene, propene, 1-butene and 2-butene. Ethene is especially preferred.

In the process according to the present invention, the carbon monoxide can be used in its pure form or diluted with an inert gas such as nitrogen, carbon dioxide or noble gases such as argon. If the ethylenically unsaturated compound is a gas, e.g. ethene, a gaseous mixture of carbon monoxide and the ethylenically unsaturated compound can be used.

For the preparation of a carboxylic anhydride, an ethylenically unsaturated compound is reacted with carbon monoxide and an appropriate carboxylic acid. Carboxylic acids which can be used as a co-reactant in this reaction preferably have from 2 to 20, more preferably from 3 to 10 carbon atoms. The carboxylic acid can be aliphatic cycloaliphatic or aromatic and is preferably aliphatic. The carboxylic acid can further be normal or branched. The carboxylic acid can comprise one or more double bonds per molecule but preferably contains no double bonds. The carboxylic acid comprises at least one carboxyl group, but can also comprise more than one carboxyl group and is for example a carboxylic di-acid. In the carboxylic acid one or more hydrogen atoms may have been replaced by other atoms, such as halogen atoms, sulphur atoms, oxygen atoms or nitrogen atoms, or by groups of atoms, such as hydroxyl groups; cyano groups; alkoxy groups, such as methoxy or ethoxy groups; thioxy groups; amino groups such as dimethyl- and diethyl-amino groups; or aromatic groups, such as phenyl, tolyl or naphthyl groups. Preferably the carboxylic acid contains no heteroatoms. Examples of carboxylic acids that can be used as a co-reactant include propanoic acid, butanoic-acid, pentanoic acid, pentenoic acid, adipic acid, hexanoic acid, heptanoic acid, cyanovaleric acid, cyclohexanoic acid, phenylpropanoic acid, malonic acid, succinic acid, or adipic acid. Propanoic acid is a preferred co-reactant.

In an especially preferred embodiment the carboxylic acid is prepared in situ by reaction of an ethylenically unsaturated compound with carbon monoxide and water.

The invention therefore also relates to a process for the preparation of a carboxylic anhydride comprising:
A) carbonylation of an ethylenically unsaturated compound with carbon monoxide and water in the presence of a catalyst to yield a carboxylic acid; and
B) carbonylation of an ethylenically unsaturated compound with carbon monoxide and the carboxylic acid obtained in step A) to yield a carboxylic anhydride as described herein.

The catalyst in step A) is preferably a catalyst comprising:
i) a source of group VIII metal;
ii) a phosphorus containing ligand; and
iii) a source of anions.

The source of group VIII metal i) is preferably a source of group VIII metal as described herein below.

The phosphorus containing ligand ii) is preferably a bidentate diphosphine. Preferred bidentate diphosphines include those described in WO-A-9842717 and WO-A-0172697 which are hereby incorporated by reference, and those bidentate diphosphines described herein below.

In step A the source of anions can be chosen from a wide range of sources, including those described in WO-A-9842717 and WO-A-0172697which are hereby incorporated by reference. Preferably, however, the carboxylic acid, as prepared in step A), is providing the complexing anions of the catalyst. Preferably no further separate source of anions is added.

Most preferably the catalyst in step A) is identical to the catalyst in step B).

By reacting an ethylenically unsaturated compound with carbon monoxide and a carboxylic acid, symmetrical carboxylic anhydrides such as for example propanoic anhydride, butanoic anhydride, hexanoic anhydride, cyclohexanoic anhydride and phenylpropanoic anhydride can be prepared, but also a-symmetrical carboxylic anhydrides such as for example acetic propanoic anhydride, butanoic hexanoic anhydride, propanoic phenylpropanoic anhydride.

The carboxylic acid co-reactant is simultaneously used to provide the complexing anions for the catalyst. When carboxylic acid co-reactant becomes depleted near the end of the reaction, appropriate amounts of the carboxylic acid, can be added to the reaction mixture. In the preparation of propanoic anhydride, the use of anions of propanoic acid as complexing anions is especially advantageous.

Therefore, in a preferred process according to the invention propanoic anhydride is prepared by reaction of ethene with carbon monoxide and propanoic acid.

The reaction is carried out in the presence of a catalyst comprising:
a) a source of a group VIII metal;
b) a bidentate diphosphine of formula I,

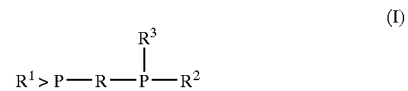

(I)

wherein $R^1$ represents a bivalent radical that together with the phosphorus atom to which it is attached is an optionally substituted 2-phospha-tricyclo[3.3.1.1{3,7})]-decyl group or a derivative thereof in which one or more of the carbon atoms are replaced by heteroatoms ("2-PA" group); wherein $R^2$ and $R^3$ independently represent univalent radicals of up to 20 atoms or jointly form a bivalent radical of up to 20 atoms; and wherein R represents a bivalent organic bridging group; and
c) a complexing anion;
wherein the complexing anion is the anion of the carboxylic acid.

Examples of group VIII metals that can be used include Ru, Rh, Ni, Pd and Pt. Preferably a source of group 10 metal is used, such as Ni, Pd or Pt. Of these, palladium and platinum are more preferred. Palladium is especially preferred.

Examples of suitable metal sources are platinum or palladium compounds such as salts of palladium or platinum and carboxylic acids with up to 12 carbon atoms, palladium- or platinum complexes, e.g. with carbon monoxide or acetylacetonate, or palladium or platinum combined with a solid material such as an ion exchanger. Palladium(II) acetate, palladium dibenzylacetone and platinum(II) acetylacetonate are examples of preferred metal sources.

The bivalent organic bridging group R in the diphosphine of formula I, preferably contains as a total in the range from 1 to 20, more preferably 2 to 10, carbon atoms. Preferably the bivalent organic bridging group R contains 1 to 6, more preferably 2 to 4 carbon atoms in the bridge, i.e. in the shortest connection between the phosphorus atoms. Preferably the bivalent organic bridging group R contains only carbon atoms in the bridge. The bridging group can be non-substituted or substituted and can contain one or more unsaturated bonds. The bridging group can further form part of an aliphatic or aromatic ring structure. Examples of possible bridging groups include substituted or non-substituted bivalent aryl groups, such as for example bivalent xylyl, tolyl or naphthyl group, or bivalent alkylene groups such as ethylene, trimethylene, tetramethylene or pentamethylene. Preferred bridging groups include ortho-xylene (also called methylene-benzene), ethylene and trimethylene groups.

$R^1$ in the diphosphine of formula I represents a bivalent radical that together with the phosphorus atom to which it is attached is an optionally substituted 2-phospha-tricyclo [3.3.1.1{3,7}]decyl group or a derivative thereof in which one or more of the carbon atoms are replaced by heteroatoms.

Tricyclo[3.3.1.1{3,7}]decane is the systematic name for a compound more generally known as adamantane. Therefore, the optionally substituted 2-phospha-tricyclo-[3.3.1.1{(3,7)}decyl group or a derivative thereof will be referred to as "2-PA" group (as in 2-phosphadamantyl group) throughout the specification.

Preferably, the 2-PA group is substituted on one or more of the 1, 3, 5 or 7 positions with a monovalent radical $R^5$ of up to 20 atoms, preferably of 1 to 10 carbon atoms and more preferably of 1 to 6 carbon atoms. Examples of $R^5$ include methyl, ethyl, propyl, phenyl, and 4-dodecylphenyl. More preferably, the 2-PA group is substituted on each of the 1, 3, 5 and 7 positions, suitably with identical radicals $R^5$, preferably methyl groups.

The 2-PA group has preferably additional heteroatoms other than the 2-phosphorus atom in its skeleton. Suitable heteroatoms are oxygen and sulphur atoms. Suitably, these heteroatoms are found in the 6, 9 and 10 positions.

The most preferred bivalent radical is the 2-phospha-1,3,5,7-tetramethyl-6,9,10-trioxadamantyl group.

If $R^2$ and $R^3$ each independently represent univalent radicals of up to 20 atoms, they preferably represent univalent radicals of in the range from 1 to 10 carbon atoms. The univalent radicals can be aliphatic, aromatic or cycloaliphatic, and can be straight or branched. The radicals can each independently comprise heteroatoms such as N, O and S, but preferably comprise only carbon atoms. Examples of univalent radicals include hydrocarbyl groups such as, for instance, methyl, ethyl, propyl, tert.-butyl, cyclohexyl, phenyl, pyridyl, and (substituted) trimethylsilyl or alkoxy groups. Alternatively, $R^2$ and $R^3$ may together form a bivalent radical, such as 1,6-hexylene, 1,3 or 1,4-cyclooctylene. Preferably, $R^2$ and $R^3$ together with the phosphorus atom form a 2-PA group as described herein before. Most preferably $R^2$ and $R^3$ together with the phosphorus atom form a 2-PA group identical to $R^1$.

An especially preferred diphosphine is a compound according to Formula II, wherein $R^5$ represents alkyl groups of 1 to 6 carbon atoms, preferably methyl.

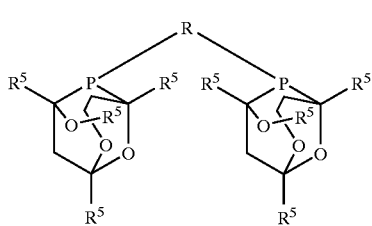

(II)

Examples of bidentate diphosphine ligands, that can be used in the process of the invention, can be found in WO-A-9842717 and WO-A-0172697 which are hereby incorporated by reference and include 1,2-P,P'-di(2-phospha-1,3,5,7-tetramethyl-6,9,10-trioxatricyclo-[3.3.1.1{3.7}decyl)-methylene-benzene (also sometimes referred to as 1,2-P,P'-di(2-phospha-1,3,5,7-tetramethyl-6,9,10-trioxatricyclo[3.3.1.1{3.7}decyl)-o-xylene); 1,2-P,P'-di-(2-phospha-1,3,5,7-tetra(ethyl)-6,9,10--trioxatricyclo [3.3.1.1{3.7}decyl)-methylene-benzene; 1,2-P,P'-di(2-phospha-1,3,5,7-tetramethyl-6,9,10-trioxatricyclo [3.3.1.1{3.7}decyl)ethane; 1,3-P,P'-di(2-phospha-1,3,5,7-tetramethyl-6,9,10-trioxatricyclo-[3.3.1.1{3.7}decyl) propane; 1,2-P,P'-di-perfluoro(2-phospha-1,3,5,7-tetramethyl-6,9,10-trioxatricyclo-[3.3.1.1{3.7}decyl) ethane, 1,3-P,P'-di-perfluoro(2-phospha-1,3,5,7-tetramethyl-6,9,10-trioxatricyclo-[3.3.1.1{3.7}decyl) propane.

Of these 1,3-P,P'-di(2-phospha-1,3,5,7-tetramethyl-6,9,10-trioxatricyclo[3.3.1.1{3.7}decyl)propane and 1,2-P,P'-di (2-phospha-1,3,5,7-tetramethyl-6,9,10-trioxatricyclo [3.3.1.1{3.7}decyl)-methylene-benzene are most preferred.

The bidentate ligands used in the process according to the invention can be prepared as described for example by Robert Pugh in his thesis "Phospha-adamantanes a new class of bulky alkyl phosphine ligands" (thesis submitted to the University of Bristol in April 2000), or as described by Ms. Victoria Gee in her thesis "Hydrophosphination as a route to novel tertiary alkyl diphosphine" (thesis submitted to the University of Bristol in 1996) or as described by Ms. Joanne H. Downing in her thesis titled "Precious metal complexes of some novel functionalised secondary and tertiary phosphines" (thesis submitted to the University of Bristol in November 1992) all of which are hereby incorporated by reference.

The bidentate ligands can be prepared in the meso- and rac-form, as described in the article titled "Tandem isomerization-carbonylation catalysis: highly active palladium (II) catalysts for the selective methoxy-carbonylation of internal alkenes to linear esters", Robert. I. Pugh et. al, Chem. Commun. 2001, pages 1476 to 1477 which is hereby incorporated by reference. The meso-form is preferred for the purpose of the present invention.

In addition to the source of group VIII metal, the bidentate diphosphine ligand and the source of anions, the catalyst can contain as an additional component a tertiary amine to further improve reaction rates. Mono-amines or poly-amines can be used, provided that the amine groups present are tertiary amine groups.

Poly-amines can contain two or more tertiary amine groups, preferably two to four tertiary amine groups, more preferably two to three amine groups and most preferably two tertiary amine groups. The nitrogen atoms in the polyamine can be substituted with an aliphatic, cycloaliphatic or aromatic group. Preferably the nitrogen atoms in the polyamine are substituted with alkyl groups, preferably containing from 1 to 10, more preferably from 1 to 4 carbon atoms. Most preferably the nitrogen atoms in the polyamine are substituted with methyl or ethyl groups. Examples of polyamines include 2,4-dimethyl-2,4-diaza-pentane, 2,5-dimethyl-2,5-diaza-hexane, 2,6-dimethyl-2,6-diaza-heptane, 2,4,6-trimethyl-2,4,6-triaza-heptane, 2,4-diphenyl-2,4-diaza-pentane, and 2-methyl-4-phenyl-2,4-diaza-pentane.

Preferably a tertiary mono-amine is used, having the formula II:

(II)

wherein N represents a nitrogen atom and $A^1$, $A^2$ and $A^3$ each independently represent an aliphatic, cycloaliphatic or aromatic group. $A^1$, $A^2$ and $A^3$ independently preferably contain in the range from 1 to 20 carbon atoms, more preferably in the range from 1 to 10 carbon atoms. More preferably at least two of $A^1$, $A^2$ and $A^3$ represent lower alkyl groups, i.e. alkyl groups having in the range from 1 to 6 carbon atoms. Examples of monoamines include trimethylamine, triethyl amine, triphenylamine, ethyldiphenylamine, and phenyldimethylamine. An especially preferred tertiary amine is triethylamine.

Carbon monoxide partial pressures in the range of 1–65 bar are preferred. In the process according to the present invention, the carbon monoxide can be used in its pure form or diluted with an inert gas such as nitrogen, carbon dioxide or noble gases such as argon. Small amounts of hydrogen can also be present.

The carbonylation reaction is conveniently carried out at moderate temperatures. Accordingly, the process is suitably carried out at a temperature in the range of 30 to 200° C., preferred temperatures being in the range of 50 to 150° C. The reaction pressures may also vary widely. For instance, the reaction can be carried out with pressures in the range of 1 to 100 bar, pressures in the range of 2 to 30 bar being preferred.

The ethylenically unsaturated compound and the carboxylic acid are suitably supplied in a molar ratio within the range of 10:1 to 1:10, preferably within the range of 5:1 to 1:5.

The quantity, in which the catalyst is used, is not critical and may vary within wide limits. Usually amounts in the range of $10^{-8}$ to $10^{-1}$, preferably in the range of $10^{-7}$ to $10^{-2}$ mole atom of group VIII metal per mole of unsaturated compound are used.

For the preparation of the catalysts of the invention, the amount of bidentate diphosphine ligand is preferably applied in some excess of the amount of the group VIII metal, expressed as moles of ligand per mole atom of the group VIII metal.

Preferably the amount of ligand is selected such that per mole atom of the group VIII metal 0.5 to 10 moles of ligand are present. However, for the preferred catalyst the active species is believed to be based on an equimolar amount of bidentate diphosphine ligand per mole group VIII metal. Thus, the molar amount of bidentate diphosphine ligand per mole of group VIII metal is preferably in the range of 1 to 3, more preferably in the range of 1 to 2. In the presence of oxygen, slightly higher amounts may be beneficial.

Now the complexing anion is provided by the carboxylic acid co-reactant, the amount of the complexing anion present can vary widely. For practical reasons the amount of complexing anion is preferably present in a molar ratio of at least 0.5 moles per mole of group VIII metal and more preferably more than 0.5 moles per mole of group VIII metal. More preferably the amount of complexing anion varies in a range from 0.5 to $10^7$, most preferably from 1 to $10^6$ moles per mole of group VIII metal.

In the process of the invention, the starting materials and the formed carboxylic anhydride may act as reaction diluent. Optionally, however, the carbonylation reaction can be carried out in the additional presence of a solvent. As such, saturated hydrocarbons such as, e.g., paraffins and isoalkanes are recommended and furthermore ethers such as 2,5,8-trioxanonane (diglyme), diethylether and anisole; sulphones such as sulpholane, and aromatic hydrocarbons such as toluene.

Preferably the carboxylic acid, used as a co-reactant is simultaneously used as a reaction diluent. Most preferably the reaction is therefore carried out in the carboxylic acid. The process according to the invention can be carried out batch-wise, semi-continuously and continuously. If the process is carried out semi-continuously, appropriate additional amounts of carbon monoxide and/or ethylenically unsaturated compound and/or carboxylic acid co-reactant are preferably added intermittently at appropriate stages in the process. Preferably the process is carried out continuously.

A carboxylic anhydride prepared by the process according to the invention can be used for various applications. In a preferred application the carboxylic anhydride is used as an acylation agent. The carboxylic anhydride can for example be used in the acylation of aromatic alcohols such as for example phenol to prepare the corresponding carboxylic ester. Another example is the acylation of amines or amides to respectively amides or imides. By acylation of diamines such as ethylene diamine and propylene diamine, bleach activators such as respectively tetra acetyl ethylene diamine and tetra acetyl propylene diamine can be prepared.

In a preferred embodiment such an acylation process is carried out with a carboxylic anhydride that is prepared in-situ.

The prepared carboxylic anhydride can also react with acetic acid in a equilibrium reaction to prepare acetic anhydride, a compound which is otherwise difficult to obtain.

The invention will now be illustrated by the following non-limiting examples.

EXAMPLE 1

The autoclave was charged 50 ml propanoic acid, 0.1 mmol.Pd(II) acetate and 0.15 mmol 1,3-PP'-di(2-phospha-1,3,5,7-tetramethyl-6,9,10-trioxatricyclo-[3.3.1.1{3.7}]decyl)propane (95% rac). After being flushed, the autoclave was next pressurized with carbon monoxide and ethene, each to a partial pressure 10 bar. Following sealing of the autoclave, its contents were heated to a temperature of 100° C. and maintained at that temperature for 5 hours. After cooling, a sample was taken from the contents of the autoclave and analysed by Gas Liquid Chromatography.

Conversion of ethene was 100% with 100% selectivity into propanoic anhydride at an average rate of 800 mole per mole Pd per hour (mol/mol Pd/hr). The average rate of reaction was defined as the mean rate of carbon monoxide consumption during a period up to the exhaustion of either one of ethene or carbon monoxide.

EXAMPLE 2

Example 1 was repeated, however with 0.15 mmol 80% meso 1,3-PP'-di(2-phospha-1,3,5,7-tetramethyl-6,9,10-trioxatricyclo[3.3.1.1{3.7}]decyl)propane instead of 0.15 mmol 95% rac 1,3-PP'-di(2-phospha-1,3,5,7-tetramethyl-6,9,10-trioxatricyclo[3.3.1.1{3.7}]decyl)propane. Ethene was fully converted with 100% selectivity into propanoic anhydride at an average rate of 2500 mol/mol.hr.

EXAMPLE 3

Example 1 was repeated, however with 0.15 mmol 0.15 mmol 1,2-PP'-di(2-phospha-1,3,5,7-tetramethyl-6,9,10-trioxatricyclo[3.3.1.1{3.7}]decyl)-methylene-benzene instead of 0.15 mmol 1,3-PP'-di(2-phospha-1,3,5,7-tetramethyl-6,9,10-trioxatricyclo[3.3.1.1{3.7}]-decyl)propane and at a process temperature of 90° C. instead of 100° C. Ethene was fully converted with 100% selectivity into propanoic anhydride at an average rate of 1000 mol/mol.hr.

COMPARATIVE EXAMPLE A

Example 1 was repeated, however with 0.2 mmol methyl sulphonic acid as an additional acid. Furthermore the autoclave was pressurized with carbon monoxide and ethene to a partial pressure of 30 and 20 bar respectively. Ethene was converted with 50% selectivity into propanoic anhydride at an average rate of 60 mol/mol.hr.

COMPARATIVE EXAMPLE B

Example 1 was repeated, however with 0.15 mmol 1,3-PP'bis(di-tert.butylphosphino)propane instead of 0.15-mmol 1,3-PP'-di(2-phospha-1,3,5,7-tetramethyl-6,9,10-trioxatricyclo[3.3.1.1{3.7}]decyl)propane and a carbon monoxide partial pressure of 15 bar instead of 10 bar. Ethene was converted with 100% selectivity into propanoic anhydride at an average rate of 120 mol/mol.hr.

EXAMPLE 4

Promotion by di-ethylamine

Example 1 was repeated, however with 0.09 mmol Pd (II) acetate, 0.1 mmol 1,3-PP'-di(2-phospha-1,3,5,7-tetramethyl-6,9,10-trioxatricyclo[3.3.1.1{3.7}]decyl)propane and in addition 2 ml diethylamine. Ethene was fully converted with 100% selectivity into propanoic anhydride at an average rate of 3700 mol/mol.hr.

EXAMPLE 5

In situ Preparation of Propanoic Acid for the Preparation of Propanoic Anhydride Example 1 was repeated, except that the propanoic acid was prepared in-situ by adding 1 ml water to the autoclave at the start and adding after 30 min, further ethene (10 bar) and carbon monoxide (10 bar) to the autoclave. Ethene and water were fully converted with 100% selectivity into propanoic anhydride at an average rate of 1000 mol/mol.hr. The average rate of reaction was defined as the mean rate of carbon monoxide consumption during a period starting after 30 min. up to the exhaustion of either one of carbon monoxide or ethene.

EXAMPLE 6

In-situ Acrylation of Butylamine

The autoclave was charged 50 ml propanoic acid, 0.1 mmol Pd(II)acetate and 0.15 mmol 1,3-PP'-di(2-phospha-1,3,5,7-tetramethyl-6,9,10-trioxatricyclo-[3.3.1.1{3.7}]decyl) propane (95% rac) and 10 ml butylamine. After being flushed, the autoclave was next pressurized with carbon monoxide and ethene, each to a partial pressure 10 bar. Following sealing of the autoclave, its contents were heated to a temperature of 100° C. and maintained at that temperature for 5 hours. Further ethene (10 bar) and carbon monoxide (10 bar) were added to the autoclave when gas neared consumption. After cooling, a sample was taken from the contents of the autoclave and analyzed by Gas Liquid Chromatography. Butylamine was fully converted (through acylation by formed propionic anhydride) into N-butylpropionamide (91%) and N-butyl-diethylcarboximide (7%) at an average rate of 2200 mol/mol.hr.

EXAMPLE 7

In-situ Acrylation of Phenol

Example 6 was repeated, however with 15 g phenol instead of 10 ml butylamine. Furthermore after 1 hour further ethene (10 bar) and CO (10 bar) were added to the autoclave. Phenol was converted (through acylation by formed propionic anhydride) with 100% selectivity to phenyl propionate at an average rate of 1500 mol/mol.hr.

We claim:

1. A process for the preparation of an carboxylic anhydride by reaction of an ethylenically unsaturated compound with carbon monoxide and an carboxylic acid in the presence of a catalyst comprising:
   a) a source of a group VIII metal;
   b) a bidentate diphosphine of formula I,

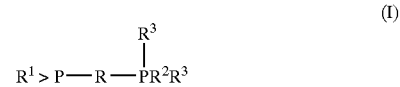

wherein $R^1$ represents a bivalent radical that together with the phosphorus atom to which it is attached is an optionally substituted 2-phospha-tricyclo[3.3.1.1{3, 7}]-decyl group or a derivative thereof in which one or more of the carbon atoms are replaced by heteroatoms ("2-PA" group); wherein $R^2$ and $R^3$ independently represent univalent radicals of up to 20 atoms or jointly form a bivalent radical of up to 20 atoms; and wherein R represents a bivalent organic bridging group; and,
   c) a complexing anion;
   wherein the complexing anion is the anion of the carboxylic acid, and wherein any additional stronger acid than the carboxylic acid is present in a molar ratio to the group VIII metal of less than 0.5:1.

2. A process of claim 1 wherein the ethylenically unsaturated compound is an alkene having from 2 to 20 carbon atoms.

3. A process of claim 2 wherein the alkene is ethene.

4. A process of claim 1 wherein carboxylic acid has from 2 to 20 carbon atoms.

5. A process of claim 4 wherein the carboxylic acid is propanoic acid.

6. A process of claim 1 wherein the bidentate diphosphine is 1,3-P,P'-di(2-phospha-1,3,5,7-tetramethyl-6,9,10-trioxatricyclo[3.3.1.1{3.7}-decyl)propane or 1,2-P,P'-di(2-phospha-1,3,5,7-tetramethyl-6,9,1 0-trioxatricyclo [3.3.1.1{3.7}decyl)-methylene-benzene.

7. A process of claim 1 wherein the catalyst contains as an additional component a tertiary amine compound.

8. A process for the preparation of a carboxylic anhydride comprising:
   a) carbonylation of an ethylenically unsaturated compound with carbon monoxide and water in the presence of a catalyst to yield a carboxylic acid; and,
   b) carbonylation of an ethylenically unsaturated compound with carbon monoxide and the carboxylic acid obtained in step a) to yield a carboxylic anhydride according to a process for the preparation of an carboxylic anhydride by reaction of an ethylenically unsaturated compound with carbon monoxide and an carboxylic acid in the presence of a catalyst comprising:
   a) a source of a group VIII metal;
   b) a bidentate diphosphine of formula I,

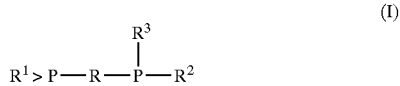

wherein $R^1$ represents a bivalent radical that together with the phosphorus atom to which it is attached is an optionally substituted 2-phospha-tricyclo[3.3.1.1{3, 7}]-decyl group or a derivative thereof in which one or more of the carbon atoms are replaced by heteroatoms ("2-PA" group): wherein $R^2$ and $R^3$ independently represent univalent radicals of up to 20 atoms or jointly form a bivalent radical of up to 20 atoms; and wherein R represents a bivalent organic bridging group; and, c) a complexing anion;

wherein the complexing anion is the anion of the carboxylic acid, and wherein any additional stronger acid than the carboxylic acid is present in a molar ratio to the group VIII metal of less than 0.5:1.

9. The process of claim 1 further comprising a step wherein the carboxylic anhydride is used in situ as acylation agent.

* * * * *